United States Patent
Hansen

(10) Patent No.: US 11,801,671 B2
(45) Date of Patent: Oct. 31, 2023

(54) METHOD FOR FABRICATION OF A TWO-LAYERED PRODUCT BASED ON ELECTROSPUN FIBRES

(71) Applicant: Afyx Therapeutics A/S, Copenhagen (DK)

(72) Inventor: Jens Hansen, Virum (DK)

(73) Assignee: AFYX THERAPEUTICS A/S, København S (DK)

( * ) Notice: Subject to any disclaimer, the term of this patent is extended or adjusted under 35 U.S.C. 154(b) by 778 days.

(21) Appl. No.: 16/479,493

(22) PCT Filed: Jan. 22, 2018

(86) PCT No.: PCT/DK2018/050009
§ 371 (c)(1),
(2) Date: Jul. 19, 2019

(87) PCT Pub. No.: WO2018/133909
PCT Pub. Date: Jul. 26, 2018

(65) Prior Publication Data
US 2019/0351662 A1  Nov. 21, 2019

(30) Foreign Application Priority Data
Jan. 23, 2017  (DK) .............................. PA 201770042

(51) Int. Cl.
*B32B 37/06* (2006.01)
*B32B 37/00* (2006.01)
(Continued)

(52) U.S. Cl.
CPC .......... *B32B 37/0053* (2013.01); *A61K 9/006* (2013.01); *A61K 9/0014* (2013.01); *A61K 9/7007* (2013.01); *B32B 37/06* (2013.01)

(58) Field of Classification Search
CPC ... B32B 37/0053; B32B 37/06; A61K 9/0014; A61K 9/006; A61K 9/7007
See application file for complete search history.

(56) References Cited

U.S. PATENT DOCUMENTS

| 4,765,983 A | 8/1988 | Takayanagi et al. |
| 7,390,760 B1 | 6/2008 | Chen et al. |

(Continued)

FOREIGN PATENT DOCUMENTS

| CA | 2134635 A1 | 5/1995 |
| CN | 102251317 A | 11/2011 |

(Continued)

OTHER PUBLICATIONS

Machine translation of JP 08216310A; Publication date: Aug. 27, 1996.*

(Continued)

*Primary Examiner* — Vishal I Patel
(74) *Attorney, Agent, or Firm* — COOLEY LLP

(57) ABSTRACT

This present invention relates to a method for making a two-layered product (3) comprising a hydrophilic first material (1) made from electrospun fibers connected to a hydrophobic second material (2) made from electrospun fibers, and wherein said first material (1) contains a drug substance, characterized in that —said method comprises using a press (5) comprising a first surface (100) and a second surface (200), and wherein said second surface (200) has a temperature being higher than the temperature of said first surface (100), —said first (1) and second material (2) being arranged in a layered combination between the first (100) and second surface (200) of the press (5), wherein a pressure is provided towards said layered combination from said first (100) and second surface (200) of said press (5), and whereby said first material (1) comes into contact with said first surface (100) of said press (5), —wherein the combination of pressure (Continued)

between the first (100) and second surface (200) and the temperature of said second material (2) connects said first (1) and second material (2) into said two-layered product (3).

25 Claims, 2 Drawing Sheets

(51) Int. Cl.
  *A61K 9/00* (2006.01)
  *A61K 9/70* (2006.01)

(56) References Cited

U.S. PATENT DOCUMENTS

| | | | |
|---|---|---|---|
| 10,052,291 | B2 | 8/2018 | Hansen et al. |
| 11,045,430 | B2 | 6/2021 | Hansen |
| 2003/0017208 | A1 | 1/2003 | Ignatious et al. |
| 2003/0044446 | A1 | 3/2003 | Moro et al. |
| 2003/0069369 | A1 | 4/2003 | Belenkaya et al. |
| 2005/0215727 | A1 | 9/2005 | Feldstein et al. |
| 2006/0013869 | A1* | 1/2006 | Ignatious .......... A61P 3/06 424/464 |
| 2006/0094320 | A1 | 5/2006 | Chen et al. |
| 2008/0160856 | A1* | 7/2008 | Chen .......... D04H 1/43838 442/341 |
| 2009/0269392 | A1 | 10/2009 | Tauber et al. |
| 2009/0296190 | A1* | 12/2009 | Anderson .......... G02F 1/155 156/60 |
| 2010/0166854 | A1 | 7/2010 | Michniak-Kohn et al. |
| 2010/0190254 | A1 | 7/2010 | Chian et al. |
| 2010/0254961 | A1 | 10/2010 | Nishio et al. |
| 2010/0323573 | A1 | 12/2010 | Chu et al. |
| 2011/0045041 | A1 | 2/2011 | Golubovic-Liakopolous et al. |
| 2011/0111012 | A1 | 5/2011 | Pepper et al. |
| 2013/0150763 | A1 | 6/2013 | Mirzaei et al. |
| 2013/0295143 | A1 | 11/2013 | Trout et al. |
| 2014/0128345 | A1 | 5/2014 | Woodrow et al. |
| 2016/0166959 | A1 | 6/2016 | Cui et al. |
| 2017/0119690 | A1 | 5/2017 | Hansen et al. |
| 2018/0221295 | A1 | 8/2018 | Hansen et al. |
| 2018/0325834 | A1 | 11/2018 | Hansen et al. |
| 2019/0254985 | A1 | 8/2019 | Hansen et al. |
| 2019/0254986 | A1 | 8/2019 | Hansen et al. |
| 2022/0105049 | A1 | 4/2022 | Hansen et al. |

FOREIGN PATENT DOCUMENTS

| | | | |
|---|---|---|---|
| EP | 2810645 A1 | 12/2014 | |
| EP | 2813212 A1 | 12/2014 | |
| EP | 2851095 A1 | 3/2015 | |
| JP | 2003-521493 A | 7/2003 | |
| JP | 2005-290610 A | 10/2005 | |
| JP | 2005-534716 A | 11/2005 | |
| JP | 2006-502136 A | 1/2006 | |
| JP | 2009-041117 A | 2/2009 | |
| JP | 2012057018 A | 3/2012 | |
| JP | 2012519559 A | 8/2012 | |
| JP | 2013521105 A | 6/2013 | |
| JP | 2013-544259 | 12/2013 | |
| JP | 2016-536305 | 11/2016 | |
| KR | 2005-0055696 A | 6/2005 | |
| KR | 10-0564366 B1 | 4/2006 | |
| RU | 94039534 A | 8/1996 | |
| RU | 2293659 C2 | 2/2007 | |
| RU | 2386539 C1 | 4/2010 | |
| RU | 110237 U1 | 11/2011 | |
| RU | 2435876 C2 | 12/2011 | |
| RU | 2487701 C2 | 2/2013 | |
| RU | 2534534 C2 | 11/2014 | |
| RU | 2553350 C2 | 6/2015 | |
| SU | 1818728 A3 | 6/1998 | |
| WO | WO 2001/27365 A1 | 4/2001 | |
| WO | WO 2001/54667 A1 | 8/2001 | |
| WO | WO 2004/014304 A2 | 2/2004 | |
| WO | WO 2004/014448 A1 | 2/2004 | |
| WO | WO 2002/076425 A2 | 10/2004 | |
| WO | WO 2006/106514 A2 | 10/2006 | |
| WO | WO-2008024141 A2 | 2/2008 | |
| WO | WO-2010094806 A2 | 8/2010 | |
| WO | WO 2010/099292 A2 | 9/2010 | |
| WO | WO-2012070028 A1 | 5/2012 | |
| WO | WO-2013188819 A2 | 12/2013 | |
| WO | WO 2014/066297 A1 | 5/2014 | |
| WO | WO 2015/189212 A1 | 12/2014 | |
| WO | WO-2015058734 A1 | 4/2015 | |
| WO | WO 2015/106342 A1 | 7/2015 | |
| WO | WO 2015/186101 A1 | 12/2015 | |
| WO | WO-2015189212 A1 * | 12/2015 | ............ A61K 31/00 |
| WO | WO-2017130141 A1 | 8/2017 | |
| WO | WO-2018033744 A1 | 2/2018 | |

OTHER PUBLICATIONS

Machine translation of JP 08216310 A; Publication date: Aug. 27, 1996; Inventor: Suzuki Migaku.*
International Search Report dated Jul. 23, 2015 in application No. PCT/EP2015/062842, 11 pages.
International Search Report issued by the International Searching Authority for Application No. PCT/EP2016/078151 dated Feb. 2, 2017, 6 pages.
Written Opinion issued by Singapore Patent Office for Application No. 11201800360Q, dated Apr. 4, 2019, 8 pages.
International Preliminary Report on Patentability in PCT/EP2016/078151 dated Oct. 19, 2017, 6 pages.
International Search Report and Written Opinion issued by the International Searching Authority for Application No. PCT/DK2018/050010, dated Mar. 27, 2018, 12 pages.
Second Written Opinion issued by the International Searching Authority for Application No. PCT/DK2018/050010, dated Dec. 19, 2018, 7 pages.
International Preliminary Report on Patentability issued by the International Searching Authority for Application No. PCT/DK2018/050010, dated Apr. 9, 2019, 11 pages.
Ignatova et al., Electrospinning of poly(vinyl pyrrolidone)-iodine complex and poly(ethylene oxide)/poly( vinyl pyrrolidone)-iodine complex—a prospective route to antimicrobial wound dressing materials European Polymer Journal, 43:1609-1623 (2007).
Son et. al., "The effects of solution properties and polyelectrolyte on electrospinning of ultrafine poly(ethylene oxide) fibers," Polymer, 45:2959-2966 (2004).
Dow Polyox product page https://www.industrialcellulosics.com/polyox 2018, retrieved Apr. 25, 2019, from https/www.industrialcellulosics.com/polyox.
Saraswathi et al., International Journal of Pharmacy and Pharmaceutical Sciences vol. 5, Suppl. 3, 423-430 (2013).
Alborzi et al., "Release of folic acid from sodium alginate-pectin-poly ethylene oxide electrospun fibers under in vitro conditions," LWT—Food Science and Technology, vol. 59, pp. 383-388 (2014).
Chou et al., "Current strategies for sustaining drug release from electrospun nanofibers," Journal of Controlled Release, vol. 220, pp. 584-591 (2015) (avail. online Sep. 2015).
Illangakoon et al., "5-Fluorouracil loaded Eudragit fibers prepared by electrospinning" International Journal of Pharmaceutics (2015) vol. 495:895-902 (2015).
Unnithan et al., "Wound-dressing materials with antibacterial activity from electrospun polyurethane-dextran nanofiber mats containing ciprofloxacin HCl." Carbohydrate Polymers, 90(4):1786-1793 (2012).
Tonglairoum et al., "Fast-Acting Clotrimazole Composited PVP/HP[beta] CD Nanofibers for Oral Candidiasis Application," Pharmaceutical Research, 31(8):1893-1906 (2014).
Wongsasulak et al., "Effect of entrapped [alpha]-tocopherol on mucoadhesivity and evaluation of the release, degradation, and swelling characteristics of zein-chitosan composite electrospun fibers," Journal of Food Engineering, 120:110-117 (2014).

(56) References Cited

OTHER PUBLICATIONS

Li et al., "Electrospun polyvinyl-alcohol nanfibers as oral fast-dissolving delivery system of caffeine and riboflavin," Colloids and Surfaces, 103:182-188 (2012).
Tyagi et al., "ElectrospunNanofiber Matrix with a Mucoadhesive Backing Film for Orarnucosal Drug Delivery," International Journal of Materials, Mechanics and Manufacturing, 2(1):81-85 (2014).
Xin et al., "Fluorescent poly(p-phenylene vinylene)/poly(ethylene oxide) nanofibers obtained by electrospinning," Journal of Polymer Research, Kluwer Academic Publishers-Consultants Bureau, NL 18(4):477-482 (2010).
Database WPI Section Ch, Week 201227 Thomson Scientific, London, GB; Class A96, An 2011-Q34326 XP002773634, Nie W; Shen X; Yu D; Zhul: "Preparation of electrospinning fiber for controlling release of alcohol-soluble medicine by dissolving zein and polyvinylpyrrolidone into ethanol aqueous solution, adding medicine, mixing, and conducting electrostatic spinning", & CN 102 251 317 A ((UYDG) Univ Dongh UA) (2011), 2 pages.
Extended European Search Report issued by the European Patent Office for Application No. 19205743.8, dated Jan. 31, 2020, 10 pages.
Santocildes-Romero et al., "Development of bioadhesive electrospun membranes for oral mucosal drug delivery," Biobarriers 2016 poster—Final, dated Mar. 7, 2016, 1 page.
Santocildes-Romero et al., "Novel Electrospun Bioadhesive Oral Patches for Mucosal Drug Delivery," EAOM 2016 Poster—Final, dated Sep. 15, 2016, 1 page.
Santocildes-Romero, et al., "Development of Electrospun Mucoadhesive Patches for Therapeutical Applications in Oral Medicine," UKSB 2017 Poster—Final, dated Jun. 20, 2017, 1 page.
Hadley et al., "Pre-clinical Evaluation of Novel Electrospun Patches for Intra-Oral Drug Delivery," A02_Murdoch Poster, dated Sep. 16, 2016, 1 page.
Colley et t al., "Adhesion and Acceptability of Novel Oral Patcheds in Human Volunteers," EAOM Poster—Final dated Sep. 15, 2016, 1 page.
Clitherow et al., "Development of Electrospun Polymer Devices for Drug Delivery to the Oral Mucosa," 2Warwickpolymerconference_KClitherow, dated Jul. 11, 2016, 1 page.
Clitherow et al., "Incorporating Antifungal Agents in Electrospun Patches to Inhibit Candida Albicans," KClitherow_PPE_China-17, dated Jul. 25, 2017, 1 page.
Avis et al., "Specificity and Mode of Action of the Antifungal Fatty Acid cis-9-Heptadecenoic Acid Produced by Pseudozyma flocculosa," Applied and Environmental Microbiology 67:956-960 (2001).
Colley et al., "Pre-Clinical Evaluation of Novel Mucoadhesive Bilayer Patches for Local Delivery of Clobetasol-17-Propionate to the Oral Mucosa," Biomaterials 178:134-146 (2018).
International Search Report and Written Opinion issued by the International Searching Authority for Application No. PCT/DK2018/050009, dated Apr. 18, 2018, 9 pages.
International Search Report and Written Opinion issued by the International Searching Authority for Application No. PCT/US20/49920, dated Dec. 4, 2020, 12 pages.
International Search Report issued by the International Searching Authority for Application No. PCT/US2020/054832, dated Jan. 18, 2021, 40 pages.
Masek et al., "Multi-layered nanofibrous mucoadhesive films for buccal and sublingual administration of drug-delivery and vaccination nanoparticles—important step towards effective mucosal vaccines", Journal of Controlled Release, Elsevier, Amsterdam, NL 249:183-195 (2017).
Santocildes-Romero et al., "Fabrication of Electrospun Mucoadhesive Membranes for Therapeutic Applications in Oral Medicine," ACS Applied Materials & Interfaces 9(13):11557-11567 (2017).
Bakyt A et al. "The development of a formulation of an adhesive matrix of a transdermal patch comprising thiamazole," Management, economy and quality assurance in pharmacy, 3:8-11 (2015).
Carbone M et al., "Systemic and topical corticosteroid treatment of oral lichen planus: a comparative study with long-term follow-up," J Oral Pathol Med 32(6):323-329 (2003).

\* cited by examiner

METHOD FOR FABRICATION OF A TWO-LAYERED PRODUCT BASED ON ELECTROSPUN FIBRES

CROSS-REFERENCE TO RELATED APPLICATIONS

This application is a U.S. National Stage Application under 35 U.S.C. § 371 of International Application No. PCT/DK2018/050009, filed Jan. 22, 2018, which claims the benefit of priority to PA 201770042, filed Jan. 23, 2017, the disclosure of each of which is hereby incorporated by reference in its entirety for all purposes.

FIELD OF THE INVENTION

The invention relates to a method for fabrication of a two-layered product comprising electrospun fibres. Said two-layered product is made from a hydrophobic material and a hydrophilic material and the product may contain a drug substance. Normally, the hydrophilic material may contain a drug substance. The two-layered product is made in a bonding process, wherein pressure and heat is applied to the two aforementioned materials. Thus, the method does not require presence of glue to fix the hydrophilic and hydrophobic material together in a layered composition.

A two-layered product made by the method disclosed herein is desirable as it reduces the complexity of the fabrication of the individual materials making up the two-layered product. The method disclosed herein is a scalable and fast technique applicable for industrial implementation, as it solely relies on bonding the two materials, described above, by the application of pressure and heat to said materials.

BACKGROUND OF THE INVENTION

PCT/EP2015/062842 discloses the fabrication of electrospun fibres using a hydrophilic polymer, a bioadhesive substance, and optionally a drug substance, for application on the skin, the lips or mucosa to deliver a specific amount of the one or more drug substances to the skin or mucosa.

In general, it is possible to provide a layered product if the individual layers all are either hydrophilic or hydrophobic. However, the present inventors have found that providing a layered product of both hydrophilic and hydrophobic layers are difficult by electrospinning. There is a need for providing such a product eg in connection with the use of layered products, where one of the surfaces must be hydrophobic and impermeable to water such as products described in PCT/EP2015/062842. The present invention addresses this need by providing a method by which electrospun hydrophilic and hydrophobic material are attached to each other.

DESCRIPTION OF THE INVENTION

The present invention is a method for combining a material as disclosed in e.g. PCT/EP2015/062842 with a hydrophobic layer. The present invention provides a two-layered product where both a hydrophilic layer and a hydrophobic layer are provided as electrospun fibres and where they are attached to each other by means of the present method, i.e. by means of pressure and a temperature difference provided to the two layers. In principle, the method of the invention can be used in the preparation of a two-layered product when the use of eg glue or other chemical means for attaching two layers are unwanted or insufficient.

The advantages of the present method is that it is possible to provide the electrospun layers independently of each other, i.e. the hydrophilic electrospun material may be provided by one electrospinning process and the hydrophobic electrospun material in another electrospinning process and the layers provided by these different (or alike) processes are brought together by the present method. The present inventors have observed that combining such two materials eg by means of a glue may change the properties of the final product in an undesired matter. Thus, if the hydrophilic layer contains a drug substance and it should be released therefrom in a specific release pattern, the use of a glue to combine the two layers may negatively influence the release. Thus, especially in designing compositions with a content of a drug substance it is important to eliminate negative influence from the ingredients and therefore there is a need for obtaining layered products without content of such ingredients.

The present method addresses this problem and provides self-adhesive layers, even between non-chemically compatible layers and between layers that do not contain specific adhesive substances, which is promoted by combination of heterogeneous heating and pressure. Without wishing to be bound by any theory, the application of critical heat at a temperature normally below the melting point of the materials and pressure promote strong adhesion due to the unique high surface to volume ratio of the electrospun fibers. It should be mentioned that a temperature near or even above the melting point of the hydrophobic fiber-forming polymers used in the hydrophobic material may be employed provided that the contact time between the heated surface and the hydrophobic material is relatively short to avoid total melting of the material or partly melting resulting in adherence to the heated surface. Thus, the present inventors have observed that using a temperature up to about 10° C. above the melting point of the hydrophobic fiber-forming polymer is possible as long as the contact time is less than about 1-3 minutes.

In the present context the term "two-layered product" is used to denote that the product is a layered product containing at least two layers, one of which being hydrophilic and the other being hydrophobic. Within the definition is also a multi-layered product, i.e. a product containing 3, 4, 5 or more layers provided that two of the layers, which are in contact with each other, are hydrophilic and hydrophobic layers. Thus, eg a product that has the following separate layers is within the definition:
  i) Hydrophobic layer
  ii) Hydrophilic layer
  iii) One or more further hydrophilic and/or hydrophobic layers and all layers are sandwiched together.

The scope of the present invention is to provide a method for bonding materials made from electrospun fibres with constituents as disclosed above into a two-layered product.

The inventors have found that a method comprising pressure and heat is suitable for fabricating a two-layered product comprising a hydrophilic first material made from electrospun fibers connected to a hydrophobic second material made from electrospun fibers, and wherein said first material may contain a drug, and said method being characterized in that said method comprises using a press comprising a first surface and a second surface, and wherein said second surface has a temperature being higher than the temperature of said first surface, said first and second material being arranged in a layered combination between the first and second surface of the press, wherein a pressure is provided towards said layered combination from said first and second surface of said press, and whereby said first material comes into contact with said first surface of said press, wherein the combination of pressure between the first and second surface and the temperature of said second material connects said first and second material into said two-layered product.

By a layered combination is meant that the first material and the second material are arranged such that their primary planes are parallel, i.e. said materials are arranged on top of each other resembling a stack or a sandwich.

By a connection between the first material and the second material is meant any kind of connection, physical and/or chemical, ensuring said materials are not separated by accident. A physical connection may be entanglement among the electrospun fibres, whereas a chemical connection may be manifested as chemical bonds. It is contemplated that the connection is established by physical connection or weak interaction at the molecular level (ion-ion interaction, van der Waal's forces).

The heating of the hydrophobic second material by the second surface increases the strength of the bonding between the hydrophilic first and hydrophobic second material. More particular, by heating the polymer of the hydrophobic second material to a temperature of below the melting point of the polymer or, alternatively, to the melting point or above, but for a relatively short time to avoid totally melting of the polymer and adherence of the polymer to the second surface. By the subsequent cooling of the two-layered product through the termination of the heating, the hydrophilic and hydrophobic electrospun layers are locked in their new position.

The hydrophilic first material may contain a drug substance according to the invention, and an increased temperature of said hydrophilic first material may alter the properties of said drug. It is therefore desirable to avoid heating of said first hydrophilic material. However, this may depend upon the drug used.

The heating means may be any means capable of heating the surfaces of the press to a predefined temperature. The heating may originate from electrical resistance, hot fluids transferring heat to the surface, or any other heating means capable of being incorporated into a press as disclosed.

The material of the surface of the press in contact with the materials to be bonded may be any material not damaging the chemical composition of the electrospun fibres. Further, a material with excellent heat capacity for transferring heat and a material capable of withstanding high pressures is desired. Therefore, metal is the preferred material, but ceramics is foreseen within the scope of the invention as well.

In an embodiment, the press is a roller press with two counter-rotating rollers, also denote calender. The rollers may be driven by any machinery commonly used in the field of such presses. The two rollers are mutual parallel and aligned to have a gap of a size facilitating the pressure needed for bonding the first and second material into the two-layered product. The surface of one of the rollers is heated to a temperature being higher than the temperature of the surface of the other roller. Due to the rollers rotating in opposite directions of each other, an input is created where the surfaces of the two rollers converge into the gap, whereas an output is created where the surfaces of the two rollers diverge out of the gap. In order to achieve the two-layered product, the hydrophobic material and the hydrophilic material are arranged in a layered combination and fed into the input, such that the hydrophobic material comes into contact with the roller having a heated surface. Due to the rotation of the rollers, the size of the gap ensuring a sufficient pressure, and the temperature of the surfaces of the rollers, the two materials are bonded into the two-layered product and led out through the output of the rollers.

In an embodiment, the press is a plate press comprising a first and a second surface being substantially flat and mutually parallel. Said two mutually parallel surfaces are capable of retracting and moving closer relative to each other. One of said surfaces are heated to a temperature being higher than the temperature of the other surface. Prior to bonding, the first hydrophilic material and the second hydrophobic material to be bonded are arranged in between the two surfaces in a layered combination with the hydrophobic material to be in contact with the heated surface. By moving the first and second surfaces mutually closer, a pressure is applied onto the layered combination, and in combination with the temperature of the surfaces, the bonding occurs. Subsequently, the parallel surfaces are retracted and the two-layered product formed from the bonding is removed from the press. The press may be driven by hydraulics, but other machine presses are foreseen within the scope of the invention.

The press may be a combination of a flat surface and a roller arranged to roll across said surface. Either the surface of the roller or the flat surface is heated to a temperature being higher than the temperature of the opposite surface. The hydrophilic first material and the hydrophobic second material is arranged in a layered combination upon the flat surface, with the second hydrophobic material in contact with the heated surface. The roller is set to roll across said layered combination, applying a pressure sufficient for bonding the first and second material into the two-layered product. Either the pressure may be applied through the roller being set to a predefined distance above the flat surface, or it may be further forced down onto the layered combination by use of external mechanics, such as hydraulics.

In an embodiment, the hydrophobic material and the hydrophilic material are shaped into sheets or layers prior to the bonding process, wherein the thickness of said sheets is significantly smaller than any other dimension of the sheets.

The thickness of the hydrophilic and hydrophobic material need not be the same. The thicker the hydrophobic layer is the less flexible it is. Thus, in order to achieve a flexible layer, the hydrophobic layer is applied with a thickness that is the same or smaller than the hydrophilic layer. In those cases, where the function of the hydrophobic layer is to keep water or body fluid to enter the hydrophilic layer from via the hydrophobic layer, the layer must be sufficiently thick and robust to withstand the impact of water or body fluid. Normally, the hydrophobic layer is present in an amount 10-50 g per $m^2$. Normally a thickness of less than 100 μm is obtained.

There may also be situations where the hydrophobic material has a larger extension than the hydrophilic material such that the hydrophobic material also covers the edges of the hydrophilic material.

In an embodiment, both the first and the second surface of the press are heated to a predefined temperature, or both surfaces may have the capability of being heated. The temperature of the surfaces possesses a temperature difference.

Hydrophilic Electrospun Layer

The hydrophilic polymer, which is the basic ingredient in the hydrophilic material, is the ingredient that has the ability to form a fibre material. In order to avoid any confusion with other ingredients present either in the electrospun fibres or in a composition thereof the term "fibre-forming hydrophilic polymer" is used. The fibre-forming hydrophilic polymer is suitably a polymer that is soluble in or forms a gel in a $C_1$-$C_3$ alkanol such as methanol, ethanol, propanol or isopropanol, notably ethanol, propanol or isopropanol, or in water mixtures thereof, where the water content is at the most 20% w/w, preferably much less such as at the most 5-10% w/w or 3-5% w/w. The spinning process requires that the polymer, which is the main component of the fibres, is in dissolved form to allow a steady stream of the dissolved polymer to flow from a needle to a grounded collecting plate in a jet-like fashion during the spinning process.

Suitable fibre-forming hydrophilic polymers are polyvinylpyrrolidone (PVP), acrylates and acrylic copolymers (eg Eudragit®), and mixtures thereof. Other polymers like eg ethylcellulose (EC), hydroxypropylcellulose (HPC), or mixtures thereof may also be used. Ethylcellulose (EC), hydroxypropylcellulose (HPC), or mixtures thereof may especially be used in combination with polyvinylpyrrolidone (PVP) and/or acrylates including acrylic copolymers (eg Eudragit®) In the examples especially PVP and acrylic copolymers have been used. Other hydrophilic polymers may be polyvinylalcohol and carboxymethylcellulose (including alkali salts thereof), and mixtures thereof.

Polyvinylpyrrolidone can be used in a grade having an approximate molecular weight of from 2,500 Da to 3,000,000 Da (eg Povidone with K-values of from 12 to 120). PVP can be purchased as Kollidon®:

| Kollidon ® | Weight average molecular weight $M_w$ |
|---|---|
| 12PF | 2,000-3,000 |
| 17PF | 7,000-11,000 |
| 25 | 28,000-34,000 |
| 30 | 44,000-54,000 |
| 90F | 1,000,000-1,500,000 |

In the low MW-range suitable grades are contemplated to have a MW of from about 25,000 to about 120,000 Da, notably from about 70,000 to about 100,000 Da. In the examples herein Koillidon® 90F has mainly been used and accordingly, a preferred PVP has a $M_w$ of from about 900,000-about 3,000,000, notably from about 1,000 to about 1,500,000.

Ethylcellulose is sold under the trademark ETHOCEL™ (Dow Chemical Company) and is available in many different grades. Dow Chemical Company produces ethylcellulose in two ethoxyl types (denoted Standard and Medium). Dependent on its ethoxyl content ethylcellulose may have different softening point and melting point temperatures. Ethylcellulose is also produced in a number of different viscosities. In the table below is given a listing of available ethylcelluloses.

| ETHOCEL polymers | | | |
|---|---|---|---|
| Product viscosity designation | Viscosity range mPa*s | Ethoxyl content % Standard 48.0-49.5 | Ethoxyl content % Medium 45.0-46.5 |
| 4 | 3-5.5 | ETHOCEL Std. 4 | |
| 7 | 6-8 | ETHOCEL Std. 7 | |
| 10 | 9-11 | ETHOCEL Std. 10 | |
| 14 | 12.6-15.4 | ETHOCEL Std. 14 | |
| 20 | 18.22 | ETHOCEL Std. 20 | |
| 45 | 41.49 | ETHOCEL Std. 45 | |
| 50 | 45-55 | | ETHOCEL Med. 50 |
| 70 | 63-77 | | ETHOCEL Med. 70 |
| 100 | 90-110 | ETHOCEL Std. 100 | ETHOCEL Med. 100 |
| 200 | 180-220 | ETHOCEL Std. 200 | |
| 300 | 270-330 | ETHOCEL Std. 300 | |
| 350 | 250-385 | ETHOCEL Std. 4 | |

In plasticized form it has excellent thermoplasticity and is useful for compositions made by molding, extrusion or lamination. Ethylcellulose is also an excellent film-former and is used in coating of eg tablets. The above-mentioned ethylcellulose qualities have an ethoxyl content of at least 45.0% and, accordingly they are soluble in ethanol and practically insoluble in water.

Acrylates and acrylic acid derivative include polymethacrylates, methacrylate copolymers, acrylic copolymers and methacrylate polymers. Preferred acrylates are those sold under the trademark EUDRAGIT®, which are soluble in ethanol, or acrylates/octaacrylamide copolymer (sold under the name DERMACRYL 79). These include EUDRAGIT®E 12.5 (amino methacrylate copolymer), EUDRAGIT® E100 (amino methacrylate copolymer; basic butylated methacrylate copolymer), EUDRAGIT®E PO ((amino methacrylate copolymer), EUDRAGIT®L 100-55, EUDRAGIT®L 100 (methacrylic acid-methyl methacrylate copolymer 1:1), EUDRAGIT®S 100 (methacrylic acid-methyl methacrylate copolymer 1:2), EUDRAGIT®RL 100, EUDRAGIT®RL 100 (ammonio methacrylate copolymer type A), EUDRAGIT®RL PO, EUDRAGIT®RS 100 (ammonio methacrylate copolymer type B), EUDRAGIT®RS PO. EUDRAGIT®E is a cationic polymer based on dimethylaminoethyl methacrylate and other neutral methacrylic acid esters: EUDRAGIT®L and S are methacrylic acid copolymers and are cationic copolymerization products of methacrylic acid and methyl methacrylate.

EUDRAGIT®RL or RS is ammonio methacrylate copolymers synthesized from acrylic acid and methacrylic acid.

EUDRAGIT® E 100 is soluble up to pH 5.5 and E 12.5 is soluble above pH 5.

EUDRAGIT® L30 D-55, L-100-55 (methacrylic acid-ethyl acrylate copolymer 1:1), L 100, L 12.5, are normally used in enteric formulations, but may be used in order to delay release of the drug substance from fibres of the invention. EUDRAGIT® L30 D-55, and L-100-55 dissolve at a pH about 5.5 and the grades L 100 and L 12.5 dissolve at pH 6 or above.

As the pH in saliva normally is about 5-6 these polymers are of interest for fibres for oral use. If sustained or prolonged release is desired polymers being soluble at lower of higher pH may be more suitable for use.

EUDRAGIT® products are also available for sustained-release formulations and such grades may be of interest to incorporate in fibres of the invention either alone or with another hydrophilic polymer. Relevant grades belong to the RL, RS, NE and NM series such as RL 100, RL PO, RL 30D, and RL 12.5, RS 100, RS PO, RS 30D, and RS 12.5, NE 30D and NE 40D, and NM 30D.

Hydroxypropylcellulose is a non-ionic water-soluble cellulose ether. It combines organic solvent solubility, thermoplasticity and surface activity and that thickening and stabilizing properties. The fibres are flexible and non-tacky at high humidity. Hydroxypropylcellulose is sold under the name KLUCEL™.

Carboxymethylcellulose is available in a broad selection of grades. The viscosity ranges from 10 to 100,000 mPa*s. It is also available as it's sodium salt with a broad range of substitution levels. Dow Chemical Company sells sodium carboxymethylcellulose under the name WALOCEL™.

Polyvinylalcohol can be used in grade having an approximately molecular weight of from 20,000 Da to 200,000 Da.

The preferred fibre-forming hydrophilic polymers are selected from PVP, hydroxypropylcellulose (HPC), acrylates and acrylic acid derivatives, and mixtures thereof.

The hydrophilic material, which is in the form of an electrospun fibrous layer, may also contain one or more drug substance, one or more bioadhesive substances, one or more pharmaceutically or cosmetically acceptable excipients. Such excipients include pH-adjusting agents, preservative, taste-masking agents, anti-oxidants, stabilisers, permeation enhancers etc. Moreover, dependent of the intended use other excipients may be present such as plasticizers, surfactants etc.

The concentration of the fibre-forming hydrophilic polymer(s) in the hydrophilic material according to the invention is normally up to 100% w/w. When other ingredients are included, the minimal concentration of the fibre-forming hydrophilic polymer(s) is generally about 25% w/w to ensure that fibres are formed containing all the ingredients. Notably, the concentration is from about 40% to about 92% w/w notably from about 50 to about 85% w/w or from about 60% to 75% w/w.

In those cases, where the composition is designed for use on a mucosal surface, it may be of interest to include a bioadhesive substance to promote adhesion to the mucosa.

If strong bioadhesion is desired, the concentration of the bioadhesive substance in the electrospun fibres must be of a relatively high concentration such as 20% w/w or more, notably 40% w/w or more. To obtain fibres with such a high content of bioadhesive substance it is necessary to select bioadhesive substances that have a low solubility in the solvent used in the electrospinning process—if they are soluble, they will swell and make the electrospinning impossible or at least very difficult.

If mild bioadhesion is desired, the concentration of the bioadhesive substance in the electrospun fibres must be of a concentration of at the most 20% w/w or less, notably 10% w/w or less.

Fibres of the invention also contain a bioadhesive substance. In order to ensure an easy manufacture of the fibres and to obtain the desired bioadhesive properties in situ after application to the mucosa, it is important that the bioadhesive in itself does not contribute significantly to the viscosity of a solution containing the fibre-forming hydrophilic polymer.

In the present context the term "bioadhesive" or "bioadhesion" indicates attachment to a specified biological location such as to the surface of the skin, a lip or a mucosal surface. A bioadhesive substance imparts bioadhesiveness to the drug-containing fibres of the invention or, in certain cases it may be included in a composition of the invention eg as a separate layer, which—after application—is the inner layer facing the skin or mucosa, i.e. the layer that is in contact with the skin or mucosa.

The bioadhesive substance for use in the present context can be selected from dextran, polyethylene oxides, alginate, tragacanth, carrageenan, pectin, gelatin, guar, xanthan, gellan, methylcellulose, hydroxypropylmethylcellulose (HPMC), carboxymethylcellulose and alkali salts thereof, polymers of acrylic acids (PAA derivatives), chitosan, lectins, thiolated polymers, polyox WSRA, PAA-co-PEG (PEG is polyethylene glycol), and mixtures thereof.

In general, it is expected that the adhesive effect of polymers increases with increasing molecular weight. Thus, in general adhesive polymers having relatively high molecular weight are preferred.

Polyethylene oxide can be used in grade having an approximate molecular weight of from 100,000 to 4,000,000. Polyethylene oxide is sold under the name POLYOX™ (Dow Chemical Company) with molecular weights ranging from 100,000 to 7,000,000 Da. In certain cases PEO with a molecular weight in the lower range is preferred such as PEO with a molecular weight in the range from 100,000 to 400,000.

Dextran can be used in grade having an approximate molecular weight of from 400,000 Da to about 2,000,000 Da.

Cellulose derivatives include hydroxypropylmethylcellulose, methylcellulose and carboxymethylcellulose.

Methylcellulose is sold under the name METHOCEL™ (Dow Chemical Company) and is available in a wide range of viscosity grades (from less than 3 to over 100,000 mPA*s).

HPMC is sold in various qualities depending on the viscosity. HPMC is sold under the names Metocel® and Klucel®. A suitable HPMC has an average molecular weight from about 80,000 to about 140,000.

Preferred bioadhesive substances are polyethylene oxides, dextrans or combinations thereof.

The hydrophilic material used in the fabrication of the two-layered product according to the invention may contain a drug substance. In principle, the drug substance may be any drug substance suitable for application to a mucosa or skin for the treatment of a disease or condition. Of particular interest are drug substances selected from drug substances, which are indicated for treatment of a disease of the skin, lip, or mucosa, or in the case, where the fibres are included in compositions for application on an internal surface as described here, the drug substance may be any drug substance that is indicated for the specific treatment. In the present context, the drug substance may be selected from drug substances, which are indicated for treatment of a disease in the oral cavity such as a drug substance that is indicated for local treatment of a disease in the oral cavity. The drug substance may be present in dissolved, undissolved or partly dissolved form dependent on the drug solubility in the hydrophilic polymer and bioadhesive substance used.

Hydrophobic Electrospun Layer

The hydrophobic material is a hydrophobic electrospun layer. Notably, it is water-impermeable eg to enable an occlusive effect and/or a protective effect against fluids such as body fluids. The latter is relevant in the case where the two-layered product is for use in particularly wet environments, where it is desirable to protect the drug substance(s) within the hydrophilic material from being dissolved into the fluids. Suitable materials for providing a water-impermeable coating include polyethylene-co-vinyl acetate, ethyl-cellulose, poly(caprolactone), carbothane or polysoftane.

As mentioned in connection with the hydrophilic material, the material may contain one or more acceptable excipients. The excipients mentioned under the hydrophilic material may also be used in the hydrophobic material and vice versa.

Besides the excipients mentioned herein before, the hydrophobic and/or hydrophilic fibres may contain a plasticizer. The plasticizer imparts a certain plasticity to the fibres, it may facilitate the manufacturing process and/or improve the flexibility and processability of the polymer(s). Examples of suitable plasticizers are citric acid esters like acetyl triethyl citrate, tributyl citrate or triethylcitrate, castor oil, diacetylated monoglycerides, dibutyl sebacate, diethyl phthalate, sorbitol, glycerol or glycerol derivatives like triacetin or tributyrin, a cellulose derivative like cellulose nitrate, glycols like polyethylene glycols notably polyethylene glycols with a molecular weight from about 100 to about 1500, polyethylene glycol monomethyl ether, propylene glycol, or mixtures thereof.

LEGENDS TO FIGURES

FIG. 1 shows a side view of a first and general method for making a two-layered product.

FIG. 2 shows a perspective view of a second and preferred method for making a two-layered product.

FIG. 3 shows a side view of the method in FIG. 2.

FIG. 4 shows a perspective view of a third method for making a two-layered product.

EXAMPLES

Figure 1:
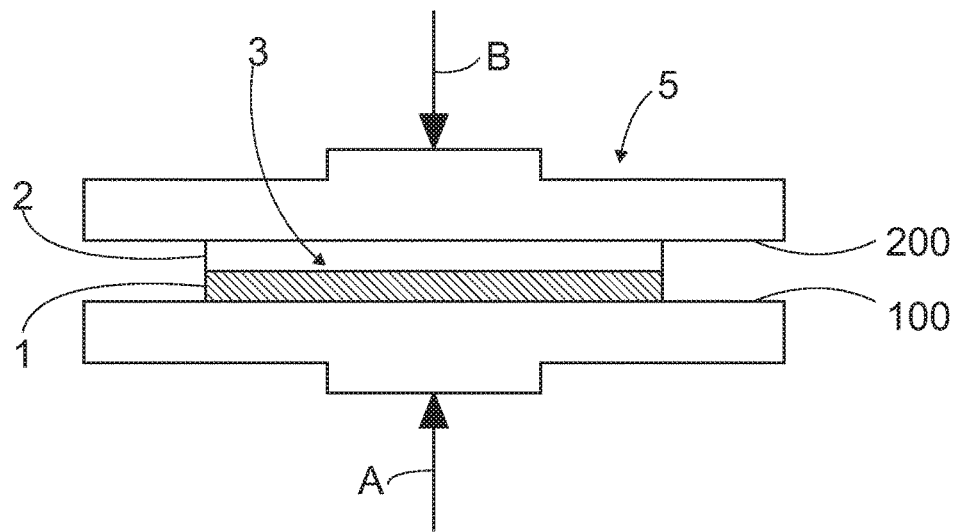
FIG. 1 shows a side view of a general method for making a two-layered product 3 using a press 5. Said press 5 comprising a first surface 100 and a second surface 200, wherein said second surface 200 is heated to a temperature being higher than the temperature of the first surface 100. The heating means is not shown. The hydrophilic material 1 and the hydrophobic material 2 are arranged within the press 5. A pressure is applied onto the two materials 1 and 2 by the two surfaces 100 and 200, in a direction indicated by the arrows A and B. One of the forces exerting the pressure may be a normal force, assuming one of the surfaces (100 or 200) are stationary.
Figure 2:
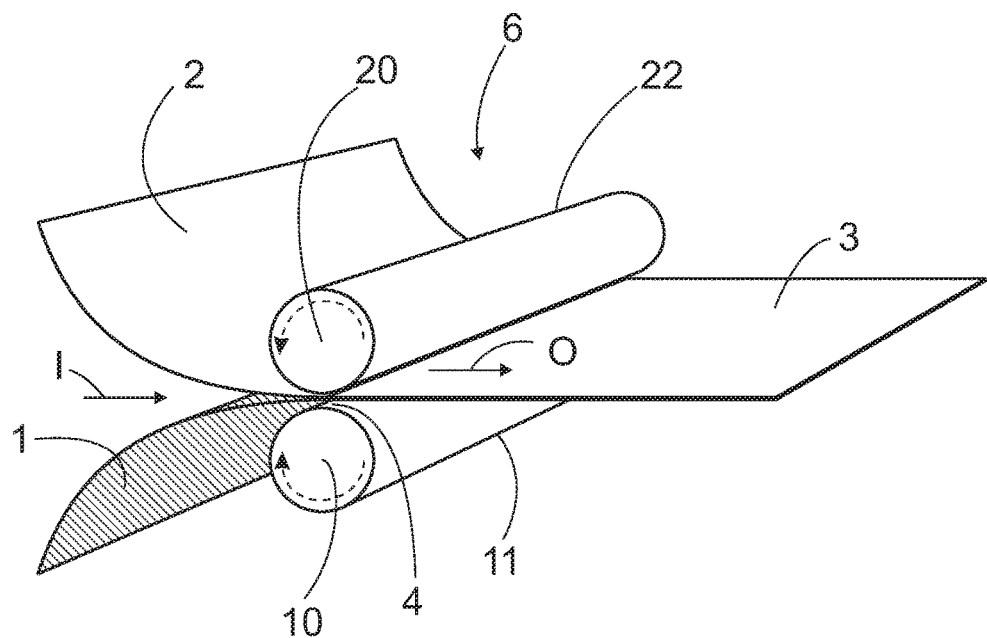
FIG. 2 shows a preferred method for making a two-layered product 3 according to the invention. The press 6 comprises a set of rollers (10, 20) being mutually parallel. The set of rollers (10, 20) comprises a first roller 10 having a first surface 11 and a second roller 20 having a second surface 22 and defines a gap 4 between the rollers (10, 20). The rollers (10, 20) rotate in opposite directions indicated by dashed arrows, such that an input I is created where the surfaces (11, 22) of the two rotating rollers (10, 20) converge, whereas an output O is created where the surfaces (11, 22) of the two rotating rollers (10, 20) diverge. The second surface 22 is heated to a temperature being higher than the temperature of the first surface 11. The heating means is not shown. A sheet of the hydrophobic material 2 and a sheet of the hydrophilic material 1 is fed into the input I, such that the hydrophobic material 2 is arranged between the heated second surface 22 and the hydrophilic material 1. Upon insertion into the input I, the rotation of the rollers (10, 20) guides the two materials (1, 2) through the gap 4, where the width of the gap 4 is of such a size as to provide a pressure from the surfaces (11, 22) of the rollers (10, 20) onto the materials (1, 2) sufficient for ensuring a bonding between the two materials (1, 2), creating the two-layered product 3 in the output O.
Figure 3:
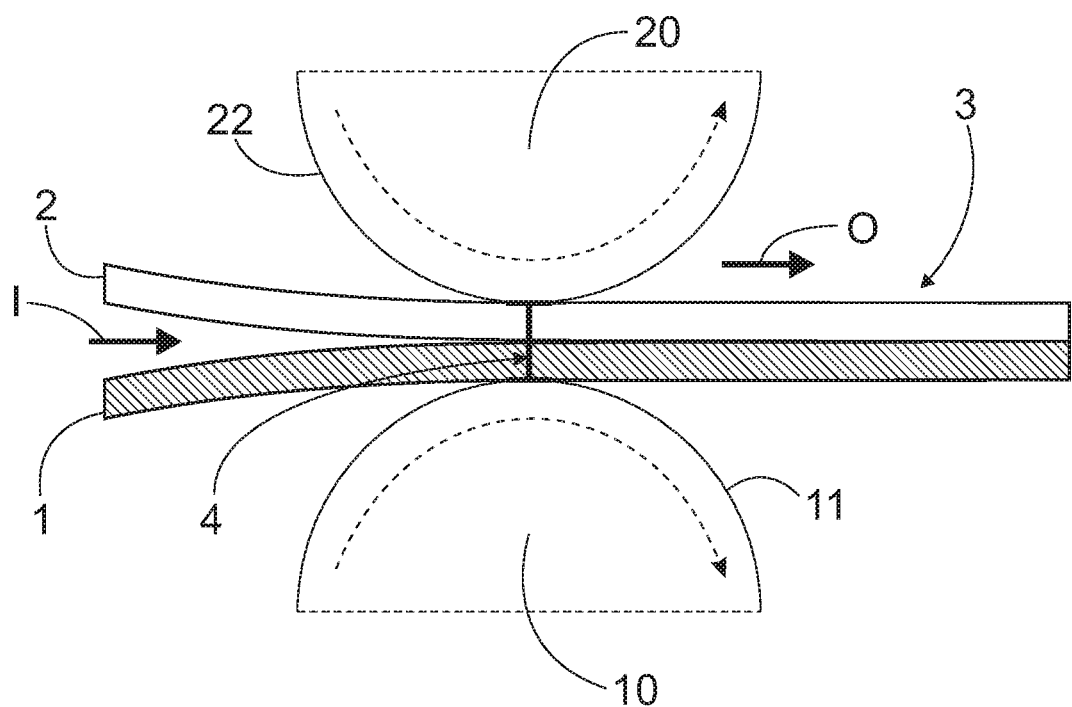
FIG. 3 shows a side view of the preferred method for making a two-layered product 3 according to the invention as described in FIG. 2. The side view focusses on the gap 4 formed between the set of two mutually parallel rollers 10 and 20. The size of the gap 4 is set to be of such a size as to ensure a pressure sufficient for bonding the first hydrophilic material 1 and the second hydrophobic material 2 into the two-layered product 3. Further mechanisms and numerals are as described in FIG. 2.
Figure 4:
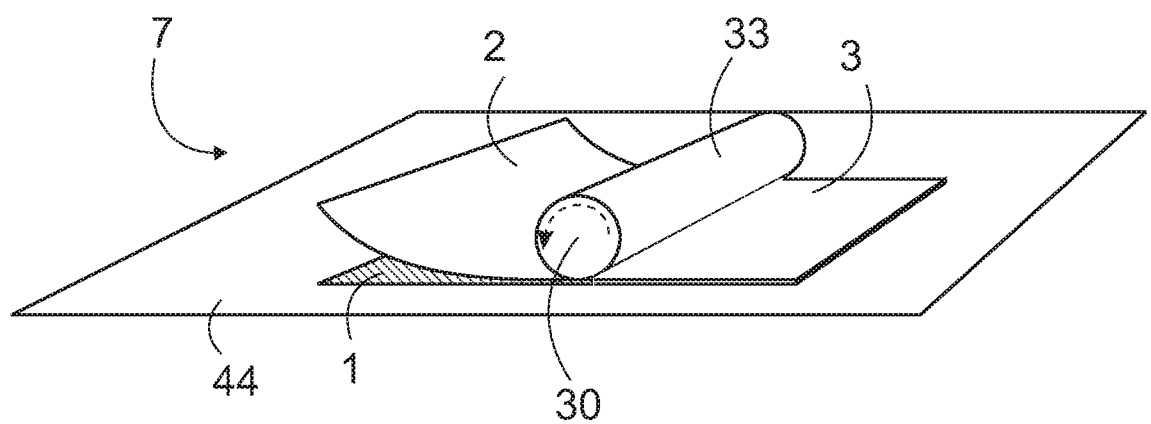
FIG. 4 shows another a press 7 comprising a roller 30 and a flat surface 44. The hydrophilic material 1 and the hydrophobic material 2 are arranged in a layered combination as shown, where the hydrophilic material 1 is in contact with the flat surface 44. The roller 30 is set to rotate according to the direction of the arrow. The surface 33 of the roller 30 is heated to a temperature being higher than the temperature of the flat surface 44. The heating means is not shown. Upon rotation of the roller 30, a pressure towards the layered combination is provided. The pressure is set to be sufficient for ensuring a bonding between the two materials (1, 2) in combination with the temperature of the flat surface 44 and the surface 33 of the roller 30. The two-layered product 3 is thereby created continuously when the roller 30 passes the sheets (1, 2). The heated surface may be interchanged, such that the flat surface 44 is heated to a temperature being higher than the temperature of the surface 33 of the roller 30. The layered combination of the hydrophilic material 1 and the hydrophobic material 2 is then likewise interchanged.

Preparation of a Two-Layer Fibrous Patch Using a Compression Hot Press.

TABLE 1

Design of experiments to improve adhesion between layers using a compression moulding hot press.

| Trial # | Patch area (m²) | Temp. PEO (° C.) | Temp. PCL (° C.) | Pressure metric ton (m.t.) | Adhesion Quality |
|---|---|---|---|---|---|
| 1 | 0.0004 | 65 | 65 | 2 | Thinning/loosing multilayer structure/Stiff |
| 2 | 0.0004 | 65 | 65 | 0 | Good adhesion/Stiff patch |
| 3 | 0.0004 | Room Temperature (RT) | 75 | 5 | Optimal adhesion and feel |

Good adhesion between the hydrophilic and hydrophobic layers was found controlling the temperature difference of the two layers. The conditions described in trial 3 were found to enhance and optimized adhesion between the two layers.

Example 2 Using an Industrial Calender

The optimized parameters for interlayer adhesion based on the learning work carried out in the Experiment 1, that allows the interlayer adhesion to be made in continuous and that scales up to an industrial process using a calender are shown in Table 2. In the calender the main working parameters are the speed at which the film is passed through the rolls and the temperature of the roll on the PCL contacting side. Good adhesion between the hydrophilic and hydrophobic layers was encountered by setting at 70° C. of the PCL side.

TABLE 2

Design of experiments to improve adhesion between membranes using calender.

| Trial # | Speed (m/min) | Temp. PEO (° C.) | Temp. PCL (° C.) | Pressure (Kg [kg/cm2]) | Adhesion quality |
|---|---|---|---|---|---|
| 1 | 2 | RT | 70 | 8 [0.5-0.8] | OK |

A person skilled in the art will know how to determine the settings of a specific calender in view of the guidance given in the examples above.

The invention claimed is:

1. A method for making a layered product comprising a hydrophilic first material and a hydrophobic second material, the method comprising:
providing a first surface and a second surface, wherein the temperature of the second surface is higher than the temperature of the first surface and:
(a) the temperature of said second surface is below the melting point of the first and second material; or
(b) the temperature of the second surface is up to about 10° C. above the melting point of the hydrophobic second material;
arranging a layered combination comprising the hydrophilic first material and the hydrophobic second material between the first surface and the second surface, whereby the hydrophilic first material comes into contact with the first surface and the hydrophobic second material comes into contact with the second surface, wherein when the temperature of the second surface is up to about 10° C. above the melting point of the hydrophobic second material, the hydrophobic second material is contacted by the second surface for less than about 3 minutes;
applying pressure towards the layered combination between the first surface and the second surface that connects the hydrophilic first material and the hydrophobic second material into the layered product, wherein the layered product comprises electrospun fibers.

2. The method of claim 1, wherein the hydrophilic first material and the hydrophobic second material are electrospun materials.

3. The method of claim 1, wherein the difference in temperature between the second surface and the first surface is at least 20° C.

4. The method of claim 1, wherein the difference in temperature between the second surface and the first surface is at the most 100° C.

5. The method of claim 1, wherein the difference in temperature between the second surface and the first surface is in a range from about 30° C. to about 60° C.

6. The method of claim 1, wherein the temperature of the first surface is about 20° C. to about 25° C. and the second surface is heated.

7. The method of claim 1, wherein the hydrophilic first material is a hydrophilic electrospun layer.

8. The method of claim 7, wherein hydrophilic electrospun layer comprises a polymer, wherein the polymer is selected from the group consisting of ethylcellulose (EC), hydroxypropylcellulose (HPC), polyvinylalcohol, carboxymethylcellulose, and mixtures thereof.

9. The method of claim 7, wherein the hydrophilic electrospun layer comprises one or more fiber-forming hydrophilic polymers.

10. The method of claim 9, wherein the fiber-forming hydrophilic polymers are selected from the group consisting of polyvinylpyrrolidone (PVP), acrylates, acrylic copolymers, and mixtures thereof.

11. The method of claim 9, wherein the one or more fiber-forming hydrophilic polymers is PVP, ammonio methacrylate copolymer type B, or mixtures thereof.

12. The method of claim 7, wherein the hydrophilic electrospun layer further comprises a drug substance.

13. The method of claim 7, wherein the hydrophilic electrospun layer further comprises a bioadhesive substance.

14. The method of claim 13, wherein the bioadhesive substance is selected from the group consisting of dextran, polyethylene oxides, alginate, tragacanth, carrageenan, pectin, gelatin, guar, xanthan, gellan, methylcellulose, hydroxypropylmethylcellulose (HPMC), carboxymethylcellulose and alkali salts thereof, polymers of acrylic acids (PAA derivatives), chitosan, lectins, thiolated polymers, polyox WSRA, PAA-co-polyethylene glycol, and mixtures thereof.

15. The method of claim 13, wherein the bioadhesive substance is polyethylene oxide, dextran, or combinations thereof.

16. The method of claim 1, wherein the hydrophobic second material comprises one or more hydrophobic polymers selected from the group consisting of polyethylene-co-vinyl acetate, ethyl cellulose, poly(caprolactone), carbothane, and polysoftane.

17. The method of claim 16, wherein the hydrophobic second material further comprises a plasticizer.

18. The method of claim 17, wherein the plasticizer is selected from the group consisting of citric acid esters, castor oil, diacetylated monoglycerides, dibutyl sebacate, diethyl phthalate, sorbitol, glycerol or glycerol derivatives, cellulose derivatives, and glycols.

19. The method of claim 1, wherein the first surface and the second surface are surfaces of a press.

20. The method of claim 19, wherein the press is a roller press.

21. The method of claim 20, wherein the roller press is a calender.

22. The method of claim 19, wherein the press is a roller press (6), the first surface is a first roller (10) and the second surface is a second roller (20), wherein the first roller and the second roller being separated by a distance defining a gap (4), wherein the layered combination is fed through the gap, the gap sized to facilitate the pressure needed for connecting the hydrophilic first material (1) and hydrophobic second material (2) into the layered product.

23. The method of claim 19, wherein the press is a plate press (5) comprising the first and the second surface, the first (100) and the second surface (200) being substantially flat and mutually parallel, and the layered combination is arranged in between said planes.

24. The method of claim 19, wherein the press (7) is a combination of a roller (30) and a flat surface (44), wherein the roller (30) rolls across the flat surface (44), upon which the layered combination is arranged, and where the roller (30) supplies a pressure ensuring bonding the hydrophilic first material (1) and hydrophobic second material (2) into the two-layered product (3).

25. A method for making a layered product comprising a hydrophilic first material and a hydrophobic second material, the method comprising:

providing a first surface and a second surface, wherein the temperature of the second surface is higher than the temperature of the first surface, wherein the difference in temperature between the second surface and the first surface is less than 100° C.;

arranging a layered combination comprising the hydrophilic first material and the hydrophobic second material between the first surface and the second surface, whereby the hydrophilic first material comes into contact with the first surface and the hydrophobic second material comes into contact with the second surface;

applying pressure towards the layered combination between the first surface and the second surface that connects the hydrophilic first material and the hydrophobic second material into the layered product, wherein the layered product comprises electrospun fibers.

* * * * *